United States Patent
Beardsley et al.

(10) Patent No.: US 11,369,378 B2
(45) Date of Patent: Jun. 28, 2022

(54) SURGICAL INSTRUMENT INCLUDING AN ADAPTER ASSEMBLY AND AN ARTICULATING SURGICAL LOADING UNIT

(71) Applicant: Covidien LP, Mansfield, MA (US)

(72) Inventors: John Beardsley, Wallingford, CT (US); Kenneth Whitfield, North Haven, CT (US); Russell Pribanic, Roxbury, CT (US); Stanislaw Kostrzewski, Newtown, CT (US); David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 75 days.

(21) Appl. No.: 16/823,901

(22) Filed: Mar. 19, 2020

(65) Prior Publication Data

US 2020/0330095 A1 Oct. 22, 2020

Related U.S. Application Data

(60) Provisional application No. 62/835,786, filed on Apr. 18, 2019.

(51) Int. Cl.
*A61B 17/072* (2006.01)
*A61B 34/30* (2016.01)
*A61B 17/00* (2006.01)

(52) U.S. Cl.
CPC ........ *A61B 17/07207* (2013.01); *A61B 34/30* (2016.02); *A61B 2017/00486* (2013.01);
(Continued)

(58) Field of Classification Search
CPC .... A61B 2017/2913; A61B 2017/2916; A61B 2017/2919; A61B 2017/00477;
(Continued)

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| AU | 2008229795 A1 | 4/2009 |
| CA | 2451558 A1 | 1/2003 |

(Continued)

OTHER PUBLICATIONS

European Search Report dated Dec. 22, 2020, issued in corresponding EP Appln. No. 20170135, 17 pages.

(Continued)

*Primary Examiner* — Stephen F. Gerrity
*Assistant Examiner* — Linda J Hodge

(57) ABSTRACT

An adapter assembly includes a cam housing defining a proximal cam slot and a distal cam slot, a first elongate shaft, and a second elongate shaft. The first elongate shaft has a proximal end portion received in the proximal cam slot, and a distal end portion configured to be coupled to a surgical loading unit. The second elongate shaft has a proximal end portion received in the distal cam slot, and a distal end portion configured to be coupled to the surgical loading unit. The first and second elongate shafts are configured to move in opposing longitudinal directions in response to a rotation of the cam housing to articulate the surgical loading unit.

17 Claims, 9 Drawing Sheets

(52) U.S. Cl.
CPC .............. *A61B 2017/07257* (2013.01); *A61B 2017/07271* (2013.01); *A61B 2017/07285* (2013.01)

(58) Field of Classification Search
CPC .. A61B 2017/00327; A61B 2017/2929; A61B 2017/2943; A61B 2017/2933; A61B 2017/0046; A61B 2017/2922; A61B 2017/2923; A61B 2017/2927; A61B 2017/07257; A61B 2017/07271; A61B 2017/07285
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A * | 7/1994 | Green .............. A61B 17/07207 227/176.1 |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |

(56) References Cited

U.S. PATENT DOCUMENTS

| | | |
|---|---|---|
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,597,104 B2 | 3/2017 | Nicholas et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |

(56) References Cited

U.S. PATENT DOCUMENTS

| | | |
|---|---|---|
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0320437 A1 | 11/2015 | Worrell et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0351747 A1* | 12/2015 | Martin ............... A61B 17/0469 606/145 |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0174971 A1* | 6/2016 | Baxter, III ........... A61B 17/105 227/176.1 |
| 2017/0224330 A1* | 8/2017 | Worthington .... A61B 17/00234 |
| 2019/0125360 A1* | 5/2019 | Shelton, IV ........... A61B 90/98 |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 B1 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| EP | 2944276 A1 | 11/2015 |
| EP | 3120780 A2 | 1/2017 |
| EP | 3205272 A1 | 8/2017 |

(56) References Cited

FOREIGN PATENT DOCUMENTS

| | | |
|---|---|---|
| EP | 3375386 A2 | 9/2018 |
| EP | 3718484 A1 | 10/2020 |
| ES | 2333509 A1 | 2/2010 |
| FR | 2861574 A1 | 5/2005 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

European Search Report dated Aug. 24, 2020, corresponding to counterpart European Application No. 20170135.6; 15 pages.

* cited by examiner

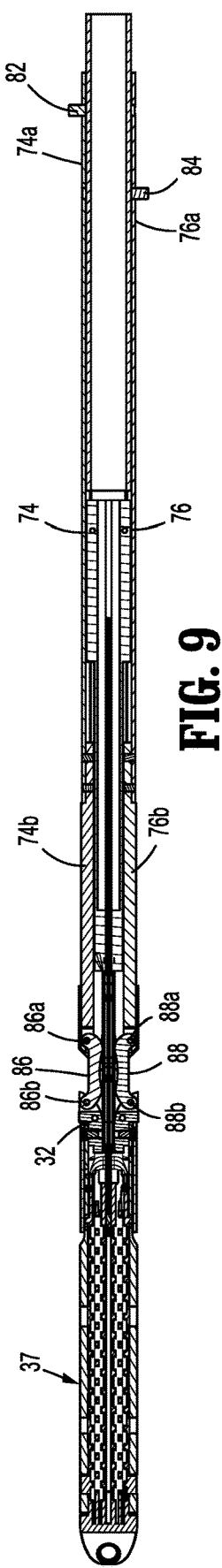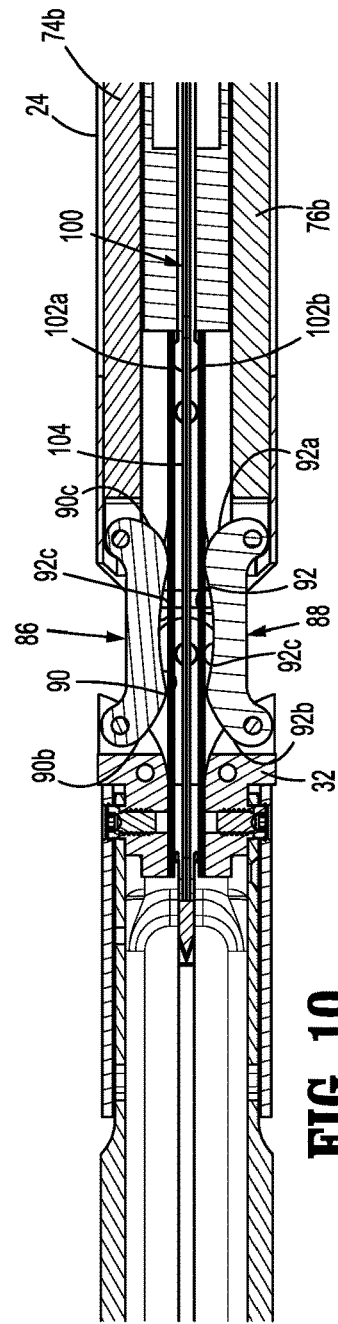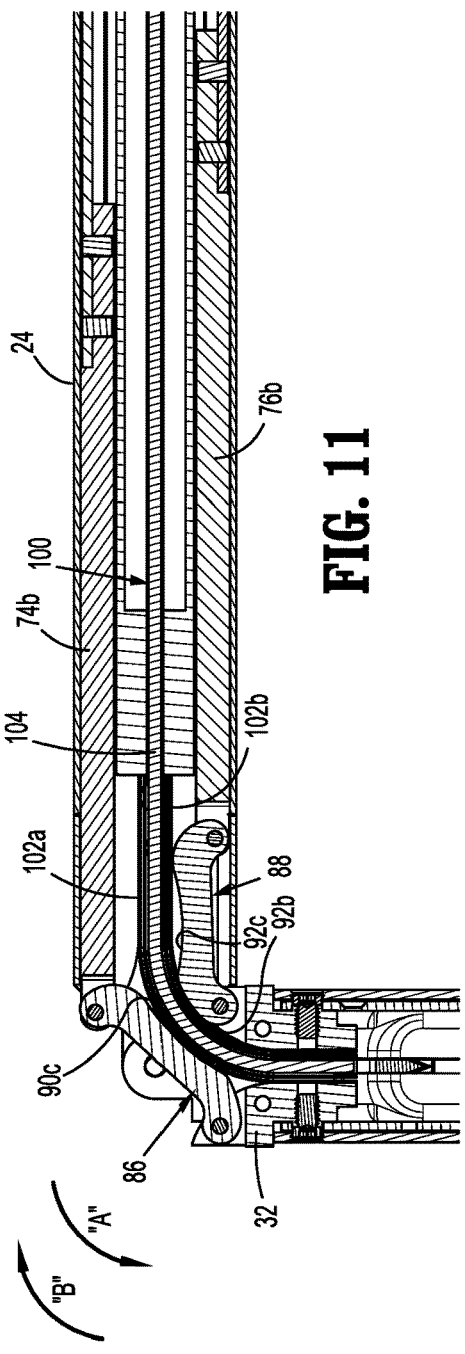
FIG. 9
FIG. 10
FIG. 11

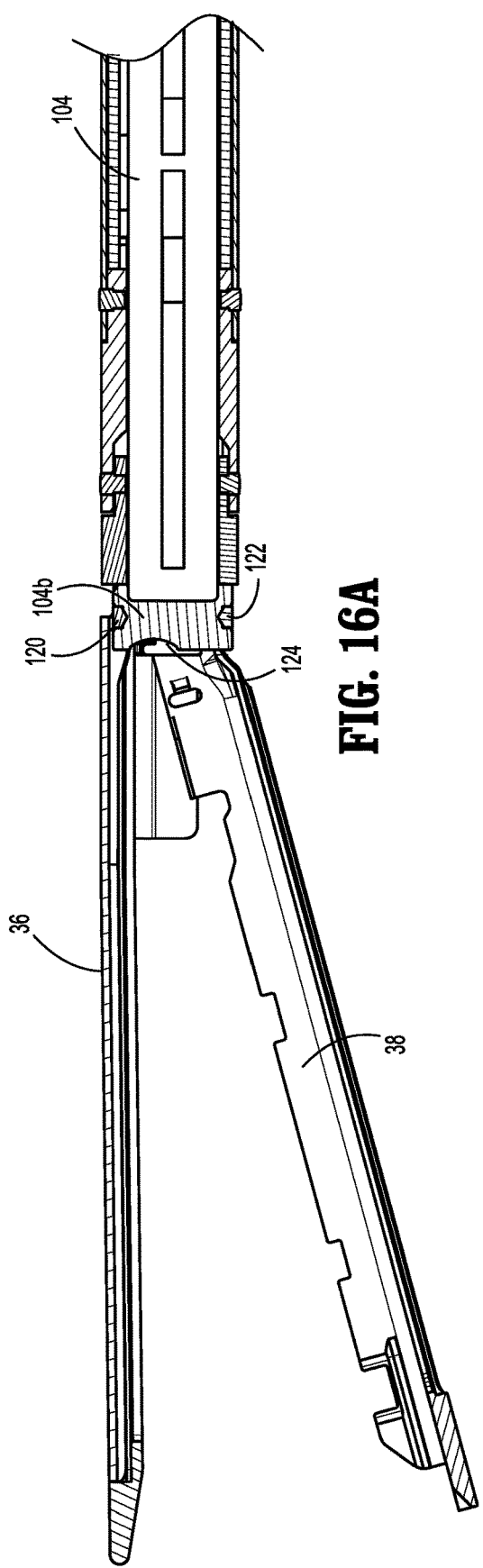
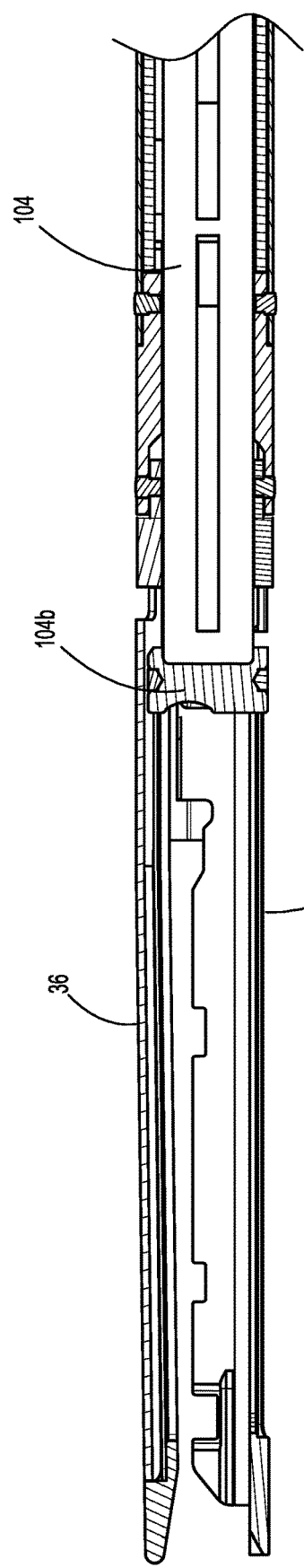

SURGICAL INSTRUMENT INCLUDING AN ADAPTER ASSEMBLY AND AN ARTICULATING SURGICAL LOADING UNIT

CROSS-REFERENCE TO RELATED APPLICATIONS

This application claims the benefit of and priority to U.S. Provisional Patent Application Ser. No. 62/835,786 filed Apr. 18, 2019, the entire disclosure of which is incorporated by reference herein.

BACKGROUND

Technical Field

The present disclosure relates generally to surgical instruments for endoscopic use and, more specifically, to surgical instruments including adapter assemblies that articulate an attached surgical loading unit.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic instruments include mechanisms for articulating the end effector of the instrument in relation to a body portion of the instrument to improve access to tissue to be treated. In addition, some end effectors have a knife shaft that translates therethrough to tissue grasped by jaws of the end effector. During articulation of the end effector, the knife shaft experiences a bending moment and/or a shear force that may degrade the knife shaft over continued articulation of the end effector.

Accordingly, it would be beneficial to provide an improved surgical instrument, which includes a mechanism for articulating the end effector relative to the body portion in a variety of orientations without damaging a knife shaft that moves through the end effector.

SUMMARY

In an aspect of the present disclosure, an adapter assembly includes a first input shaft, a cam housing operably coupled to the first input shaft and defining a proximal cam slot and a distal cam slot, a first elongate shaft, and a second elongate shaft. The first elongate shaft has a proximal end portion received in the proximal cam slot, and a distal end portion configured to be coupled to a surgical loading unit. The second elongate shaft has a proximal end portion received in the distal cam slot, and a distal end portion configured to be coupled to the surgical loading unit. The first and second elongate shafts are configured to move in opposing first and second longitudinal directions in response to a rotation of the cam housing to articulate the surgical loading unit.

In aspects, the proximal cam slot may have one of a right-handed helical configuration or a left-handed helical configuration, and the distal cam slot has the other of the right-handed helical configuration or the left-handed helical configuration.

In some aspects, the adapter assembly may further include a first link and a second link. The first link may have a proximal end portion pivotably coupled to a distal end portion of the first elongate shaft, and a distal end portion configured to be pivotably coupled to the surgical loading unit. The second link may have a proximal end portion pivotably coupled to a distal end portion of the second elongate shaft, and a distal end portion configured to be pivotably coupled to the surgical loading unit, such that the first and second links articulate the surgical loading unit in response to an actuation of the first input shaft.

In further aspects, the first and second elongate shafts may be disposed on opposite sides of a central longitudinal axis defined by the cam housing.

In other aspects, the cam housing may include a tubular shaft defining a longitudinally-extending channel. The proximal and distal cam slots may be defined in the tubular shaft.

In aspects, the proximal and distal cam slots may be disposed around a central longitudinal axis defined by the tubular shaft of the cam housing.

In some aspects, the proximal and distal cam slots may be longitudinally spaced from one another.

In further aspects, the adapter assembly may further include a ring gear operably coupled to the first input shaft and fixed to the cam housing, such that a rotation of the first input shaft results in a rotation of the cam housing.

In other aspects, the adapter assembly may further include a spur gear cluster operably coupling the ring gear and the first input shaft.

In aspects, the first elongate shaft may have a pin extending laterally from the proximal end portion thereof into the proximal cam slot, and the second elongate shaft may have a pin extending laterally from the proximal end portion thereof into the distal cam slot.

In some aspects, the adapter assembly may further include an outer housing having the first input shaft and the cam housing rotationally supported therein, and an outer tube extending distally from the outer housing. The outer tube may have the first and second elongate shafts axially supported therein.

In further aspects, the adapter assembly may further include a second input shaft extending through the cam housing and configured to effect a clamping and firing of the surgical loading unit.

In other aspects, the adapter assembly may further include a nut disposed within the cam housing and threadedly coupled to the second input shaft, and a knife shaft having a proximal end portion coupled to the nut and a distal end portion configured to cut tissue. The nut may be configured to distally move the knife shaft in response to a rotation of the second input shaft.

In aspects, the adapter assembly may further include a firing rod having a proximal end portion fixed to the nut, and a distal end portion fixed to the proximal end portion of the knife shaft. The second input shaft may extend through the firing rod.

In another aspect of the present disclosure, a surgical instrument is provided and includes an adapter assembly and a surgical loading unit. The adapter assembly includes a first axially movable elongate shaft, a second axially movable elongate shaft, a first link, and a second link. The first link has a proximal end portion pivotably coupled to a distal end portion of the first elongate shaft, and the second link has a proximal end portion pivotably coupled to a distal end portion of the second elongate shaft. The surgical loading unit has a proximal end portion pivotably coupled to a distal end portion of the first link and a distal end portion of the second link, such that the first and second links articulate the surgical loading unit in response to longitudinal motion of the first and second elongate shafts.

In aspects, the first link may include an inner surface facing the second link and having a concave intermediate portion.

In some aspects, the inner surface of the first link may have a convex proximal end portion and a convex distal end portion. The intermediate portion may be disposed between the proximal and distal end portions of the inner surface of the first link.

In further aspects, the surgical instrument may further include an axially movable I-beam assembly disposed between the first and second links. The intermediate portion of the inner surface of the first link may be dimensioned to receive a first lateral side of the I-beam assembly upon the surgical loading unit articulating relative to the adapter assembly in a first direction.

In other aspects, the surgical loading unit may include an anvil plate and a staple cartridge chassis pivotably coupled to the anvil plate. The I-beam assembly may have a distal end portion slidably coupled to both the anvil plate and the staple cartridge chassis, such that distal movement of the I-beam assembly pivots the staple cartridge chassis toward the anvil plate.

In aspects, the second link may include an inner surface facing the first link and having a concave intermediate portion dimensioned to receive a second lateral side of the I-beam assembly upon the surgical loading unit articulating relative to the adapter assembly in a second direction, opposite the first direction.

BRIEF DESCRIPTION OF THE DRAWINGS

Surgical instruments including embodiments of the presently disclosed adapter assemblies are disclosed herein with reference to the drawings, wherein:

FIG. 9 is a top, cross-sectional view of a distal section of the adapter assembly and the surgical loading unit of FIG. 1;

FIG. 10 is an enlarged, top, cross-sectional view of the adapter assembly and surgical loading unit of FIG. 9;

FIG. 11 is a top, cross-sectional view of the distal section of the adapter assembly and the surgical loading unit of FIG. 9, with the surgical loading unit illustrated in an articulated position relative to the adapter assembly;

FIG. 16A is a side, cross-sectional view of the surgical loading unit in an open configuration, illustrating the I-beam assembly in a retracted position;

FIG. 16B is a side, cross-sectional view of the surgical loading unit in a closed configuration, illustrating the I-beam assembly in an advanced position;

DETAILED DESCRIPTION

Persons skilled in the art will understand that the adapter assemblies and surgical loading units specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term "distal" refers to that portion of the surgical instrument which is farthest from a clinician, while the term "proximal" refers to that portion of the surgical instrument which is closest to the clinician. In addition, as used herein, the term clinician refers to medical staff including doctors, nurses and support personnel.

The present disclosure is directed to a surgical instrument including an adapter assembly configured to be actuated by a hand-held actuator or a surgical robotic system, and a surgical loading unit coupled to the adapter assembly. The adapter assembly includes an articulation mechanism that drives an articulation of the surgical loading unit relative to the adapter assembly. The articulation mechanism includes a cam housing that defines a pair of cam slots, each of which receiving a corresponding pin of a pair of elongate shafts. As the cam housing rotates, the cam slots drive an opposing longitudinal motion of the pair of elongate shafts, which articulate the surgical loading unit. Additional advantages of the presently disclosed surgical instruments and components thereof are described below.

Figure 1:
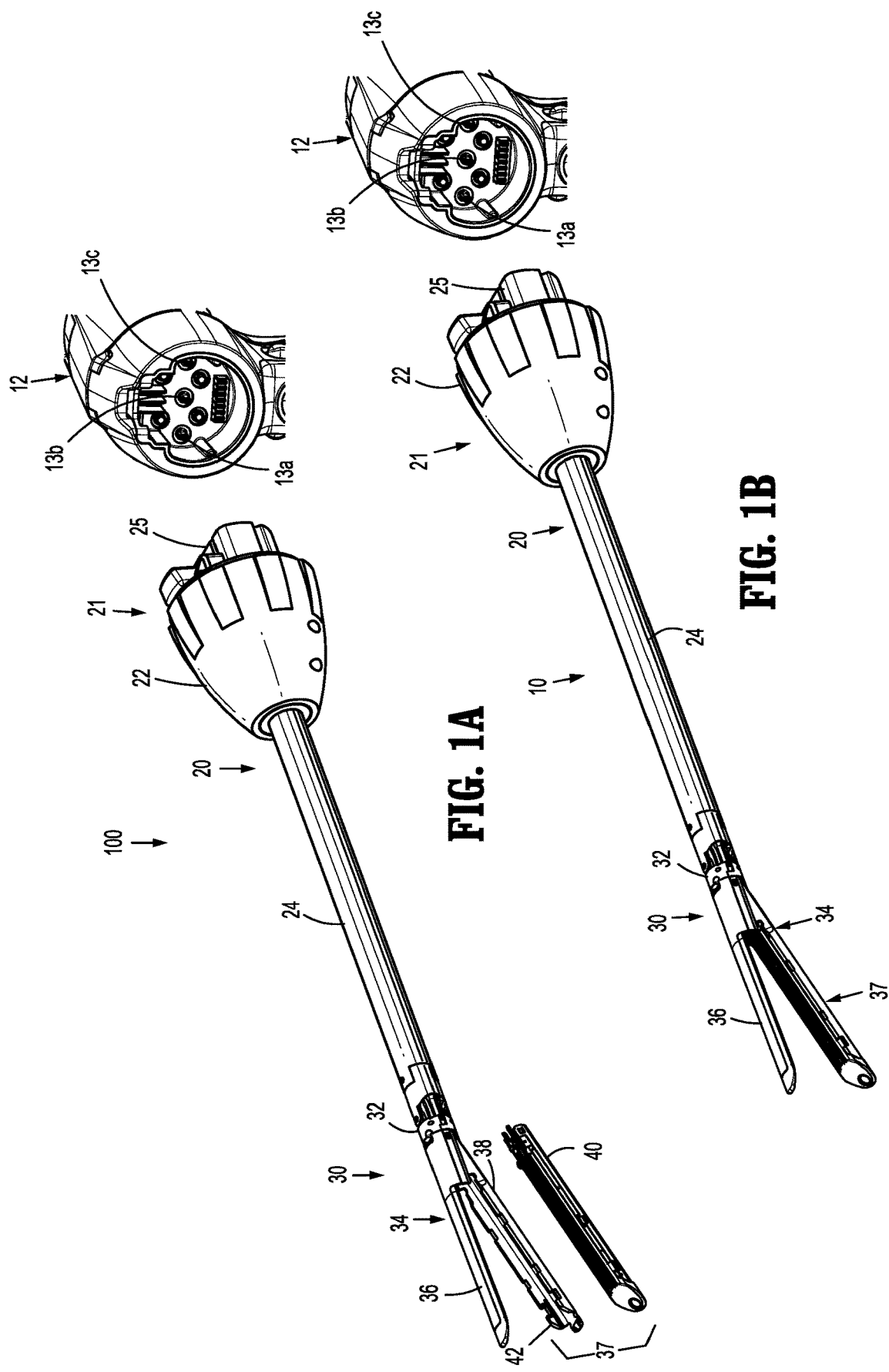
FIG. 1A is a perspective view of a surgical instrument including an adapter assembly and a surgical loading unit, with a staple cartridge body of the surgical loading unit shown removed from a chassis of the surgical loading unit.
FIG. 1B is a perspective view of the surgical instrument of FIG. 1A, with the staple cartridge body of the surgical loading unit shown installed in the chassis.

FIGS. 1A and 1B illustrate a surgical instrument 10 including a handle assembly 12, an adapter assembly 20 configured to be coupled to the handle assembly 12, and a surgical loading unit 30 pivotably coupled to the adapter assembly 20. While the depicted surgical instrument 10 may be configured to fire staples, it is contemplated that the surgical instrument 10 may be adapted to fire any other suitable fastener such as clips and two-part fasteners. Additionally, while the figures depict a linear surgical stapling instrument 10, it is envisioned that certain components described herein may be adapted for use in other types of endoscopic surgical instruments including non-linear surgical stapler loading units, endoscopic forceps, graspers, dissectors, other types of surgical stapling instruments, powered vessel sealing and/or cutting devices, etc.

Generally, the adapter assembly 20 of the surgical instrument 10 includes an outer housing 21 and an outer tube 24 extending distally from the outer housing 21. The outer housing 21 includes a knob housing 22 and a coupling mechanism 25 extending proximally from the knob housing 22 and configured to be operably coupled to the handle assembly 12 or a surgical robotic system (not shown) responsible for actuating the surgical instrument 10. The outer tube 24 has a proximal end portion fixed within the distal end portion of the knob housing 22. In other embodiments, the outer tube 24 may be rotatable relative to and within the knob housing 22. The surgical loading unit 30 is adapted to be attached to a distal end portion of the outer tube 24 of the adapter assembly 20 and may be configured for a single use, or may be configured to be used more than once.

The surgical loading unit 30 includes a collar 32 pivotably coupled to the distal end portion of the outer tube 24 and an end effector 34 supported on the collar 32. The end effector 34 includes an anvil plate 36 non-rotationally coupled to the collar 32, and a staple cartridge assembly 37 disposed in opposed relation with the anvil plate 36. The staple cartridge assembly 37 has a chassis 38 pivotably coupled to the collar 32 and a staple cartridge body 40 configured for removable receipt in a channel 42 of the chassis 38.

For a detailed description of the handle assembly 12, reference may be made to U.S. Patent Application Publication No. 2015/0157320, filed on Nov. 21, 2014, and U.S. Patent Application Publication No. 2016/0310134, filed on Apr. 12, 2016, the entire contents of each of which being incorporated by reference herein.

Figure 2:
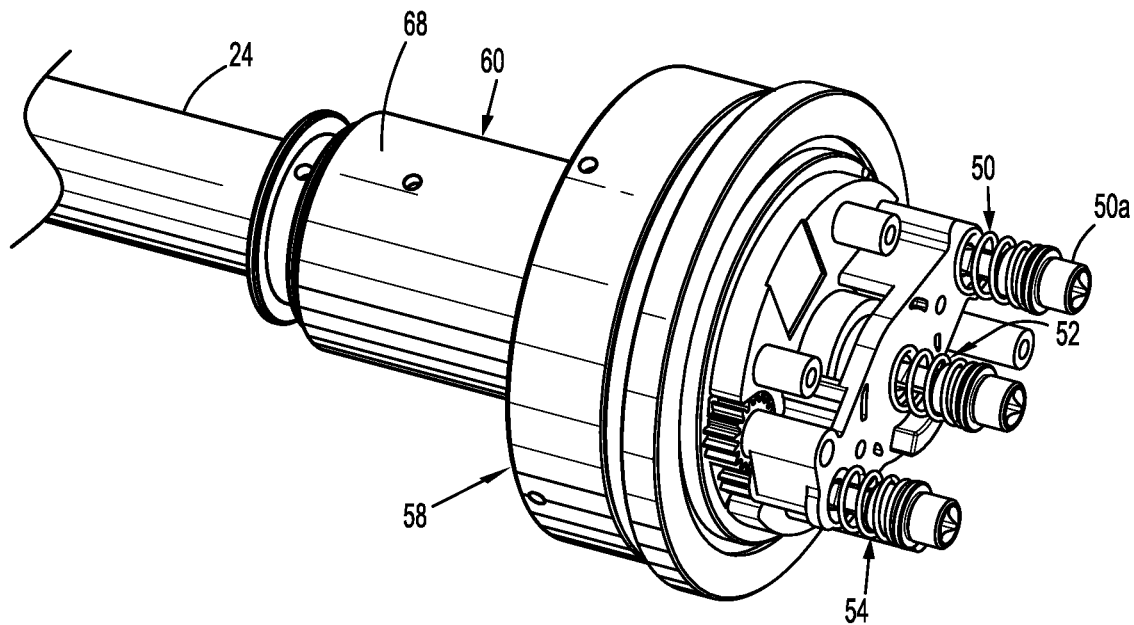
FIG. 2 is a perspective view of internal components of the adapter assembly of FIG. 1A.
Figure 3:
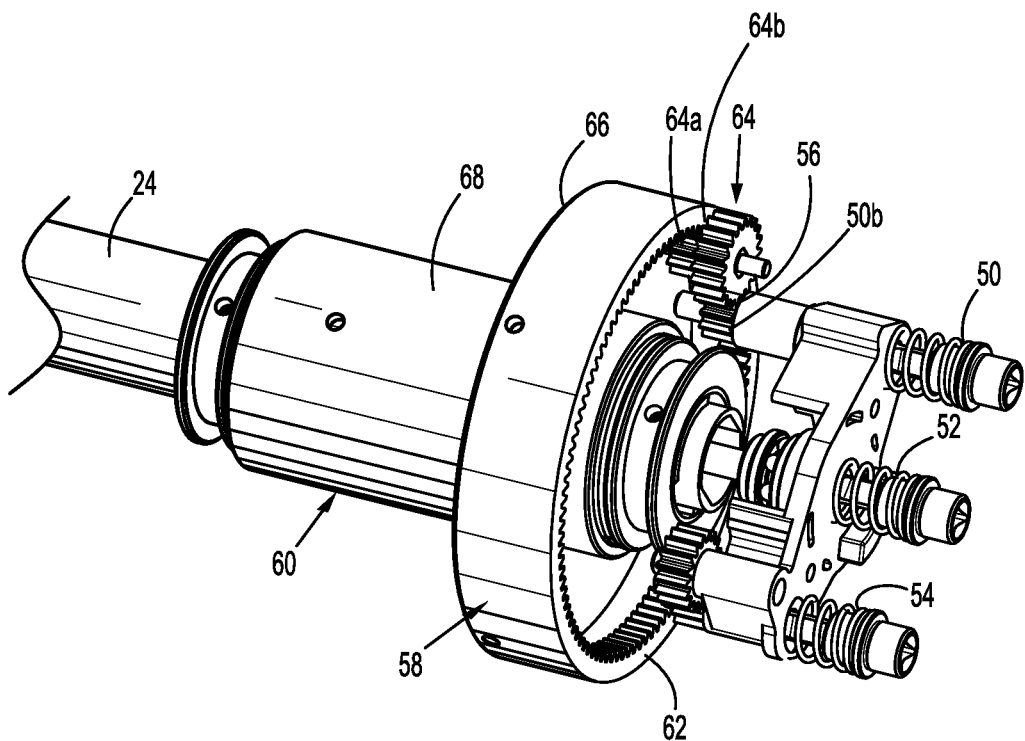
FIG. 3 is a perspective view, with parts removed, of the internal components of the adapter assembly shown in FIG. 2.
Figure 4:
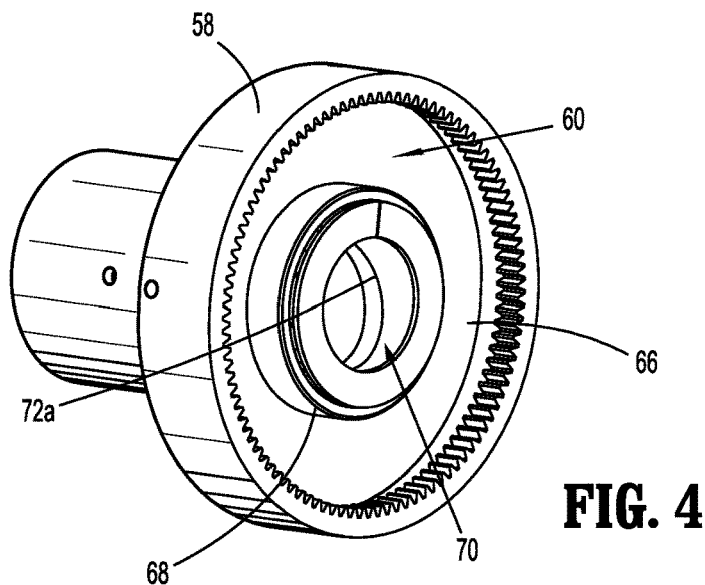
FIG. 4 is a rear, perspective view of a cam housing and a ring gear of the internal components of the adapter assembly of FIG. 2.
Figure 5:
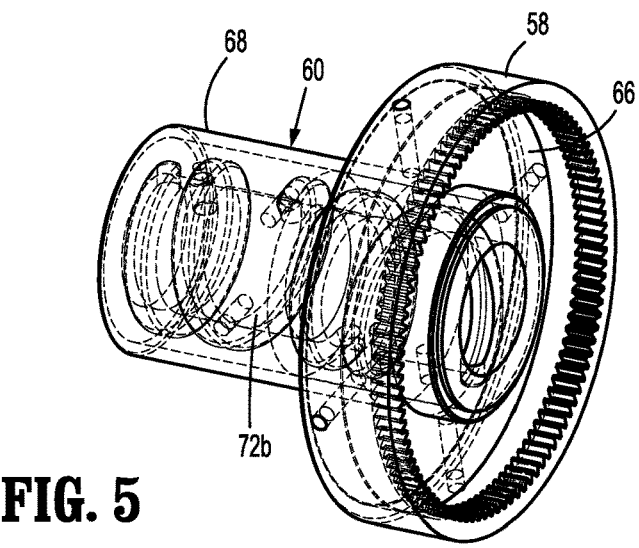
FIG. 5 is a side, perspective view of the cam housing and ring gear of FIG. 4 shown in phantom.
Figure 6:
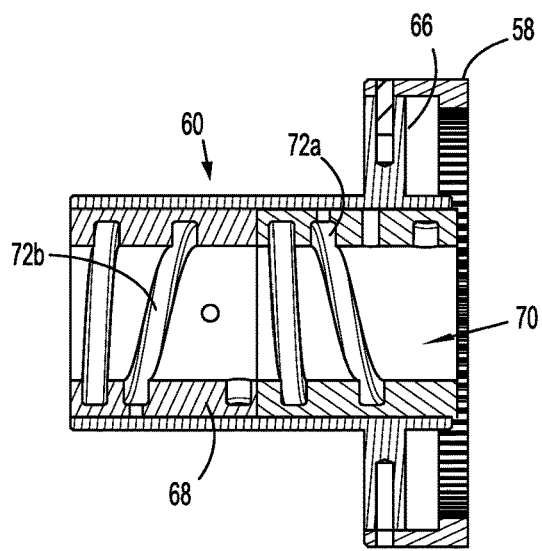
FIG. 6 is a side, cross-sectional view of the cam housing and ring gear of FIG. 4.
Figure 7:
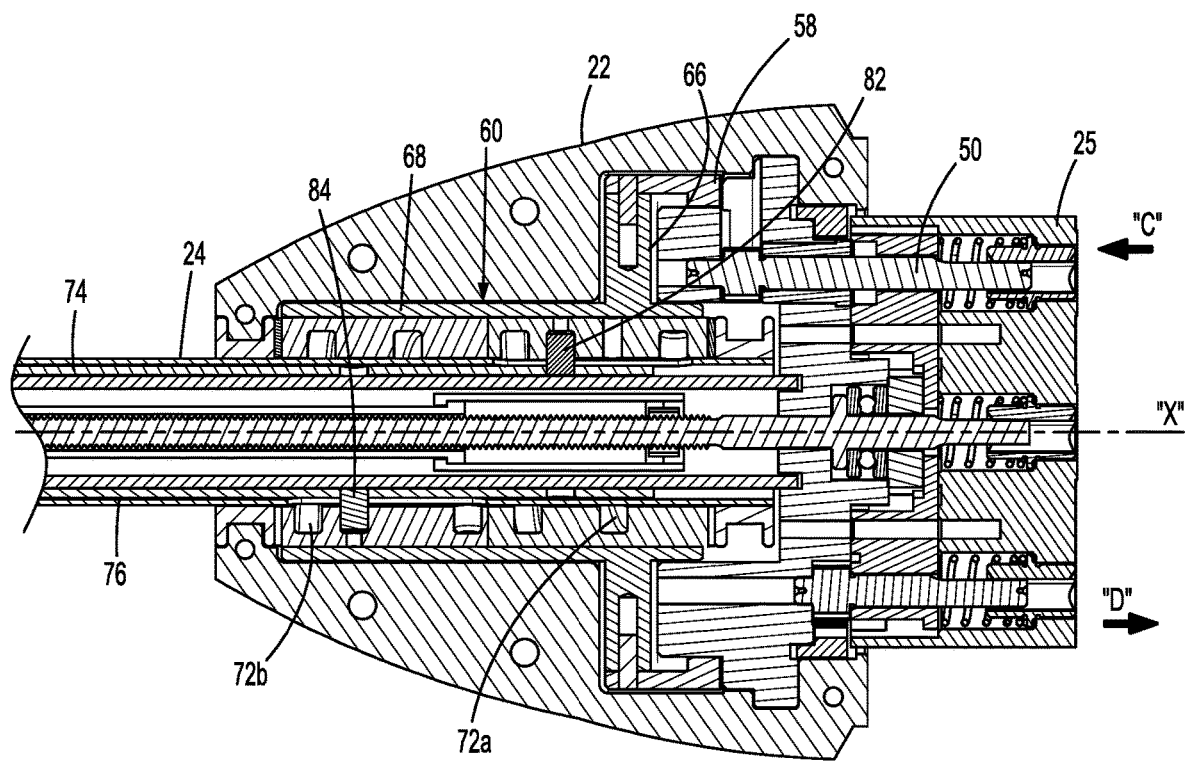
FIG. 7 is a side, cross-sectional view of a proximal section of the adapter assembly of FIG. 1A.
Figure 8:
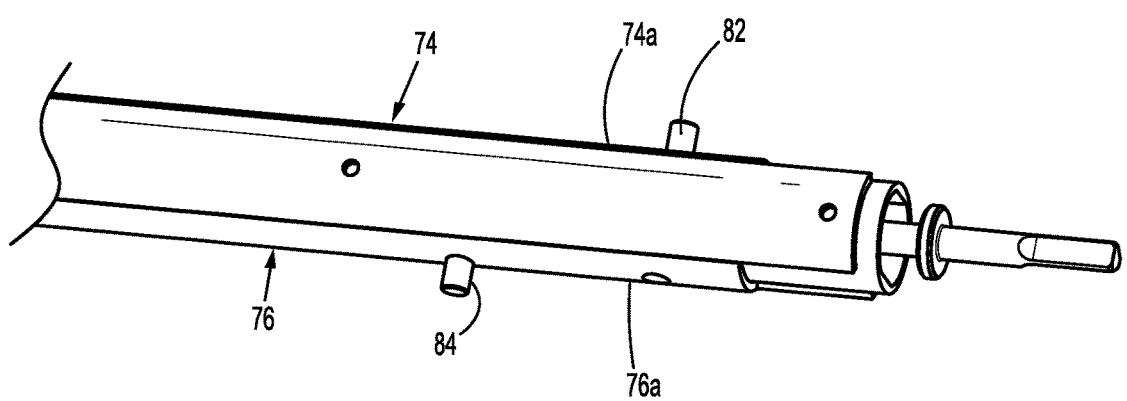
FIG. 8 is a side, perspective view of a pair of first and second elongate shafts of the adapter assembly of FIG. 7.
Figure 12:
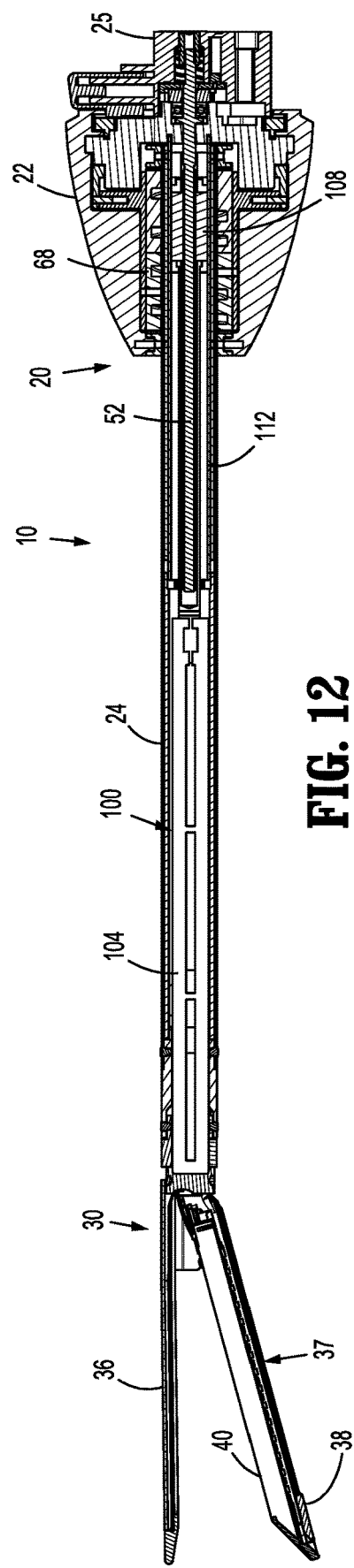
FIG. 12 is a side, cross-sectional view of the adapter assembly of FIG. 1A.
Figure 13:
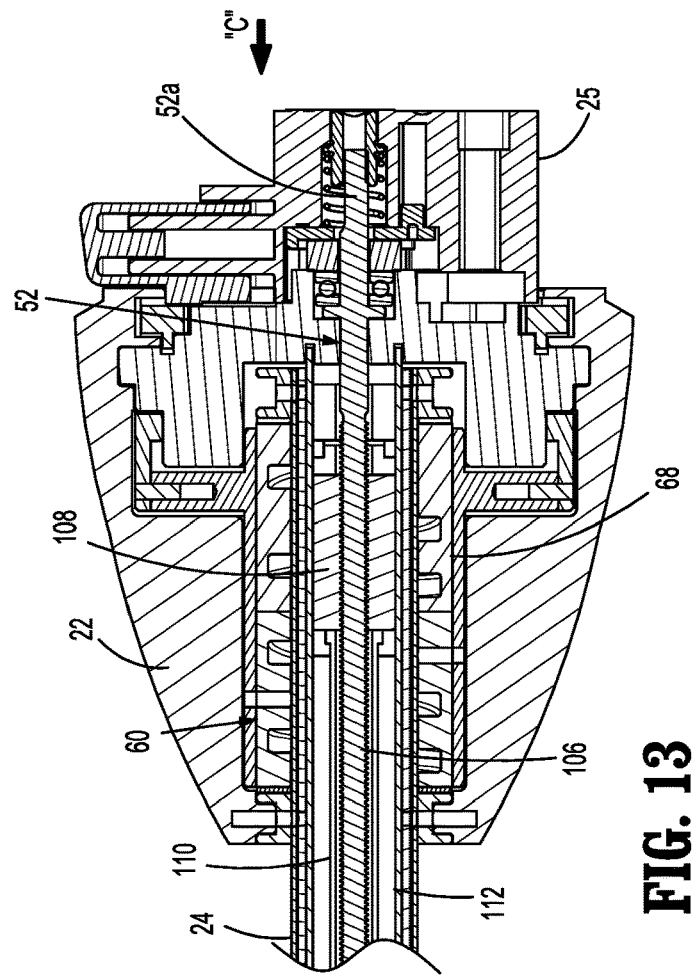
FIG. 13 is a side, cross-sectional view of the proximal section of the adapter assembly of FIG. 12.
Figure 14:
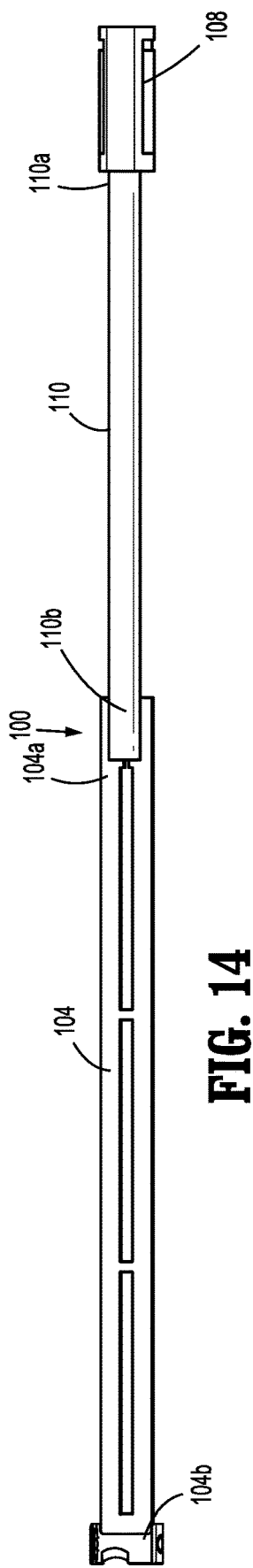
FIG. 14 is a side view of an I-beam assembly of the adapter assembly of FIG. 12.

With reference to FIGS. 2 and 3, the articulation mechanism of the adapter assembly 20 will now be described. The adapter assembly 20 includes an articulation input shaft 50, a firing input shaft 52, and a rotation input shaft 54 each rotationally supported in the coupling mechanism 25 of the outer housing 21 (FIG. 1A). The articulation input shaft 50 has a proximal end portion 50a configured to be drivingly coupled to a corresponding drive member 13a of the handle assembly 12 to effect a rotation of the articulation input shaft 50. The articulation input shaft 50 has a distal end portion 50b having a gear 56 (e.g., a spur gear) fixed thereabout.

The adapter assembly 20 includes a ring gear 58 operably coupled to the articulation input shaft 50 and non-rotationally coupled to a cam housing 60. The ring gear 58 has an inner surface defining gear teeth 62 interfacing with gear teeth of a first gear 64a of a spur gear cluster 64. The spur gear cluster 64 has a second gear 64b fixed to and disposed adjacent the first gear 64a and having a larger diameter than the first gear 64a. The second gear 64b of the spur gear cluster 64 interfaces with the gear 56 non-rotationally fixed about the distal end portion 50b of the articulation input shaft 50. As such, a rotation of the articulation input shaft 50 rotates the first gear 64a and second gear 64b of the spur gear cluster 64, which, in turn, drives a rotation of the ring gear 58.

With reference to FIGS. 2-7, the cam housing 60 of the adapter assembly 20 is rotationally supported in the knob housing 22. The cam housing 60 includes an annular plate or disc 66 and a tubular shaft 68 extending distally from the annular plate 66. The annular plate 66 may be disposed within, and pinned to, the ring gear 58, such that the cam housing 60 rotates with a rotation of the ring gear 58. The tubular shaft 68 of the cam housing 60 defines a longitudinally-extending channel 70 therethrough. The channel 70 is dimensioned for receipt of various components of the articulation and firing mechanisms of the adapter assembly 20, thereby allowing for a more compact design of the adapter assembly 20.

With reference to FIGS. 4-7, the tubular shaft 68 of the cam housing 60 defines a proximal cam slot 72a in communication with the channel 70, and a distal cam slot 72b located distally of the proximal cam slot 72a and in communication with the channel 70. The proximal and distal cam slots 72a, 72b are longitudinally spaced from one another and wrap around a central longitudinal axis "X" (FIG. 7) defined by the channel 70 of the tubular shaft 68 of the cam housing 60. The proximal and distal cam slots 72a, 72b each have opposite helical configurations. For example, the proximal cam slot 72a may have a left-handed helical configuration, whereas the distal cam slot 72b may have a right-handed helical configuration, the importance of which being described in detail below.

The proximal and distal cam slots are longitudinally spaced from one another such that at least a majority of the proximal cam slot is disposed proximally of a proximal end of the distal cam slot.

With reference to FIGS. 7-11, the adapter assembly 20 further includes a pair of first and second axially movable elongate shafts 74, 76 and a pair of first and second articulation links 86, 88. The first and second elongate shafts 74, 76 are disposed on opposite sides of the central longitudinal axis "X" of the cam housing 60. Each of the first and second elongate shafts 74, 76 has a proximal end portion 74a, 76a disposed within the knob housing 22, and a distal end portion 74b, 76b disposed within the outer tube 24.

The proximal end portion 74a of the first elongate shaft 74 has a radially-outwardly extending projection or pin 82 received within the proximal cam slot 72a. The proximal end portion 76a of the second elongate shaft 76 has a radially-outwardly extending projection or pin 84 received in the distal cam slot 72b. Due to the proximal and distal cam slots 72a, 72b of the cam housing 60 having opposing helical configurations (e.g., right-handed vs. left-handed threading), rotation of the cam housing 60 drives the first and second elongate shafts 74, 76 in opposing longitudinal directions.

The first articulation link 86 of the surgical instrument 10 has a proximal end portion 86a pivotably coupled to the distal end portion 74b of the first elongate shaft 74, and the second articulation link 88 has a proximal end portion 88a pivotably coupled to the distal end portion 76b of the second elongate shaft 76. The first and second links 86, 88 each have a distal end portion 86b, 88b pivotably coupled to opposite sides of the collar 32 of the surgical loading unit 30. As such, the opposing longitudinal motion of the first and second elongate shafts 74, 76, induced by a rotation of the cam housing 60, pushes and pulls the corresponding first and second links 86, 88 to articulate the surgical loading unit 30 relative to the adapter assembly 20.

With specific reference to FIGS. 10 and 11, the first articulation link 86 includes an inner-facing surface 90 and the second articulation link 88 includes an inner-facing surface 92 that faces the inner-facing surface 90 of the first link 86. The inner-facing surface 90 of the first link 86 has a concave intermediate portion 90c disposed between a convex proximal end portion 90a of the inner-facing surface 90 and a convex distal end portion 90b of the inner-facing surface 90. Similarly, the inner-facing surface 92 of the second link 88 has a concave intermediate portion 92c disposed between a convex proximal end portion 92a of the inner-facing surface 92 and a convex distal end portion 92b of the inner-facing surface 92. The inner-facing surfaces 90, 92 of the first and second links 86, 88 are configured to guide and support blow-out plates 102a, 102b and a knife shaft 104 of an I-beam assembly 100 of the adapter assembly 20 during articulation of the surgical loading unit 30. While intermediate portions 90c and 92c ore shown as concave, it has been found that straight or convex intermediate portions may also support blow-out plates 102a and 102b depending on the desired support and restraint at different articulation positions.

In particular, the concave intermediate portion 90c of the inner-facing surface 90 of the first link 86 is dimensioned to receive a first blow-out plate 102a of the I-beam assembly 100 during articulation of the surgical loading unit 100 in a first direction, indicated by arrow "A" in FIG. 11, whereas the concave intermediate portion 92c of the inner-facing surface 92 of the second link 88 is dimensioned to receive a second blow-out plate 102b of the I-beam assembly 100 during articulation of the surgical loading unit 100 in a second direction, indicated by arrow "B" in FIG. 11.

The convex distal end portions 90b, 92b of the inner-facing surfaces 90, 92 of the first and second links 86, 88 further support the blow-out plates 102a, 102b and the knife shaft 104 of the I-beam assembly 100 during articulation of the surgical loading unit 30. In this way, the inner-facing surfaces 90, 92 of the respective first and second links 86, 88 accommodate the flexing of the knife shaft 104 and blow-out plates 102a, 102b as the surgical loading unit 30 articulates to resist wear and tear of the knife shaft 104 and the blow-out plates 102a, 102b. For example, as best shown in FIG. 11, articulation of the surgical loading unit 30 in the first direction causes the knife shaft 104 and the blow-out plates 102a, 102b to assume a curved shape, whereby the outer blow-out plate (e.g., the first blow-out plate 102a) is guided and supported by the concave intermediate portion 90c of the inner-facing surface 90 of the first link 86, and the inner blow-out plate (e.g., the second blow-out plate 102b) is guided and supported by the convex distal end portion 92b of the inner-facing surface 92 of the second link 88. As can be appreciated, during articulation of the surgical loading unit 30 in the second direction, the first and second links 86, 88 work together in a similar manner to accommodate a flexing of the blow-out plates 102a, 102b and the knife shaft 104.

In operation, to articulate the surgical loading unit 30, the articulation input shaft 50 is rotated via an actuation of the handle assembly 12. The articulation input shaft 50 transfers rotational motion from the gear 56 fixed thereabout to the ring gear 58 via the spur gear cluster 64. Since the cam housing 60 is fixed to the ring gear 58, the cam housing 60 rotates with the ring gear 58 about the central longitudinal axis "X." As the cam housing 60 rotates, the proximal cam slot 72a of the cam housing 60 drives the pin 82 of the first elongate shaft 74 through the proximal cam slot 72 in a distal direction, indicated by arrow "C" in FIG. 7, and the distal cam slot 72b of the cam housing 60 drives the pin 84 of the second elongate shaft 76 through the distal cam slot 72b in a proximal direction, indicated by arrow "D" in FIG. 7.

Due to the first articulation link 86 acting as a pivotable coupling between the first elongate shaft 74 of the adapter assembly 20 and the first side of the surgical loading unit 30, and the second link 88 acting as a pivotable coupling between the second elongate shaft 76 of the adapter assembly 20 and the second side of the surgical loading unit 30, distal movement of the first elongate shaft 74 and proximal movement of the second elongate shaft 76 drives an articulation of the surgical loading unit 30 in the first direction indicated by arrow "A" in FIG. 11. Similarly, proximal movement of the first elongate shaft 74 and distal movement of the second elongate shaft 76 drives an articulation of the surgical loading unit 30 in the second direction indicated by arrow "B" in FIG. 11.

With reference to FIGS. 12-16, the firing and clamping mechanism of the adapter assembly 20 will now be described. The firing input shaft 52 of the adapter assembly 20 is centrally located between the articulation and rotation input shafts 50, 54 and is configured to effect a clamping and stapling function of the surgical loading unit 30. The firing input shaft 52 has a proximal end portion 52a configured to be drivingly coupled to the drive member 13b of the handle assembly 12 to drive a rotation of the firing input shaft 52. It is contemplated that the firing input shaft 52 may be configured as a drive screw having a threaded outer surface 106.

The adapter assembly 20 further includes an I-beam assembly 100, briefly described above, having a nut 108, a firing rod or tube 110, and a knife shaft 104. The nut 108 of the I-beam assembly 100 is disposed within the tubular shaft 68 of the cam housing 60 and is keyed to an inner tube 112, such that rotation of the nut 108 within the inner tube 112 is prevented during rotation of the firing input shaft 52. The nut 108 being disposed within the cam housing 60 of the articulation mechanism gives the adapter assembly 20 a compact design.

The firing rod 110 of the I-beam assembly 100 has a proximal end portion 110a fixed to the nut 108, and a distal end portion 110b fixed to a proximal end portion 104a of the knife shaft 104 of the I-beam assembly 100. In embodiments, the nut 108 may be directly attached to the proximal end portion 104a of the knife shaft 104 rather than be coupled via the firing rod 110. Since the knife shaft 104 of the I-beam assembly 100 is fixed to the nut 108, axial movement of the nut 108 through the outer tube 24, in response to a rotation of the firing input shaft 52, drives an axial movement of the knife shaft 104.

Figure 15:
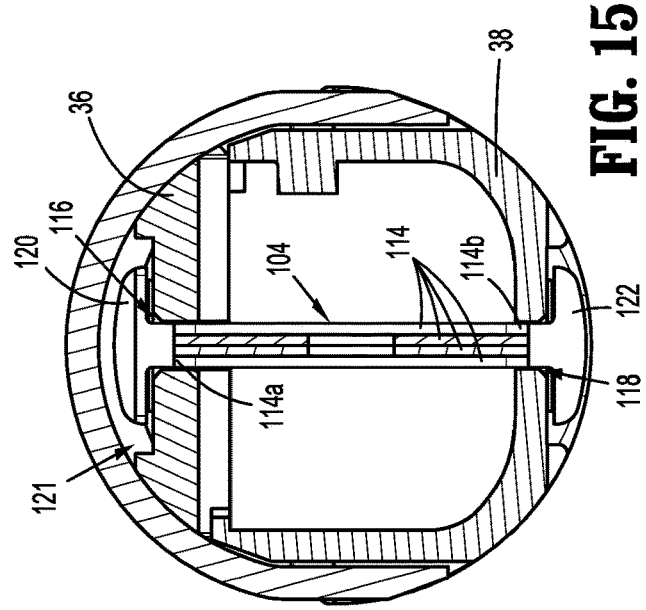
FIG. 15 is a front, cross-sectional view of the surgical loading unit and the I-beam assembly of FIG. 14.

With reference to FIGS. 15, 16A, and 16B, the knife shaft 104 of the I-beam assembly includes a plurality of stacked elongated, rectangular blades 114. The plurality of blades 114 have an upper portion 114a extending through a longitudinally-extending slot 116 defined in the anvil plate 36, and a lower portion 114b extending through a longitudinally-extending slot 118 defined in the chassis 38 of the staple cartridge assembly 37. As shown in FIG. 15, the upper portion 114a of the blades 114 overlap with the anvil plate 36, and the lower portion 114b of the blades 114 overlap with the chassis 38. It has been found that this overlapping arrangement is critical and prevents buckling of the knife shaft 104 during firing.

The knife shaft 104 of the I-beam assembly 100 has a distal end portion 104b disposed within the surgical loading unit 30. The distal end portion 104b of the knife shaft 104 is configured to pivot the staple cartridge assembly 37 toward the anvil plate 36 during distal advancement of the knife shaft 104. The distal end portion 104b of the knife shaft 104 has an upper foot 120 disposed within a channel 121 defined by the anvil plate 36, a lower foot 122 disposed outside of the chassis 38 of the staple cartridge assembly 37, and a sharp distally-oriented surface 124 extending between the upper and lower foots 120, 122. The distally-oriented surface 124 is configured to sever tissue during distal advancement thereof through the end effector 34.

In operation, to fire and clamp the surgical loading unit 30, the firing input shaft 52 is rotated via an actuation of the handle assembly 12 attached to the coupling mechanism 25 of the adapter assembly 20. The firing input shaft 52 drives a translation of the nut 108 in a distal direction, indicated by arrow "C" in FIG. 13, relative to the firing input shaft 52. Given that the I-beam assembly 100, including the nut 108, the firing rod 110, and the knife shaft 104, is one integral unit, the firing rod 110 and the knife shaft 104 advance distally with the nut 108. The distal end portion 104b of the knife shaft 104 of the I-beam assembly 100 advances distally through the anvil plate 36 and the chassis 38 to pivot the chassis 38 toward the anvil plate 36. As the distal end portion 104b of the knife shaft 104 advances distally through the anvil plate 36 and the chassis 38, any tissue disposed therebetween is severed by the sharp, distally-oriented surface 124 of the knife shaft 104.

Figure 17:
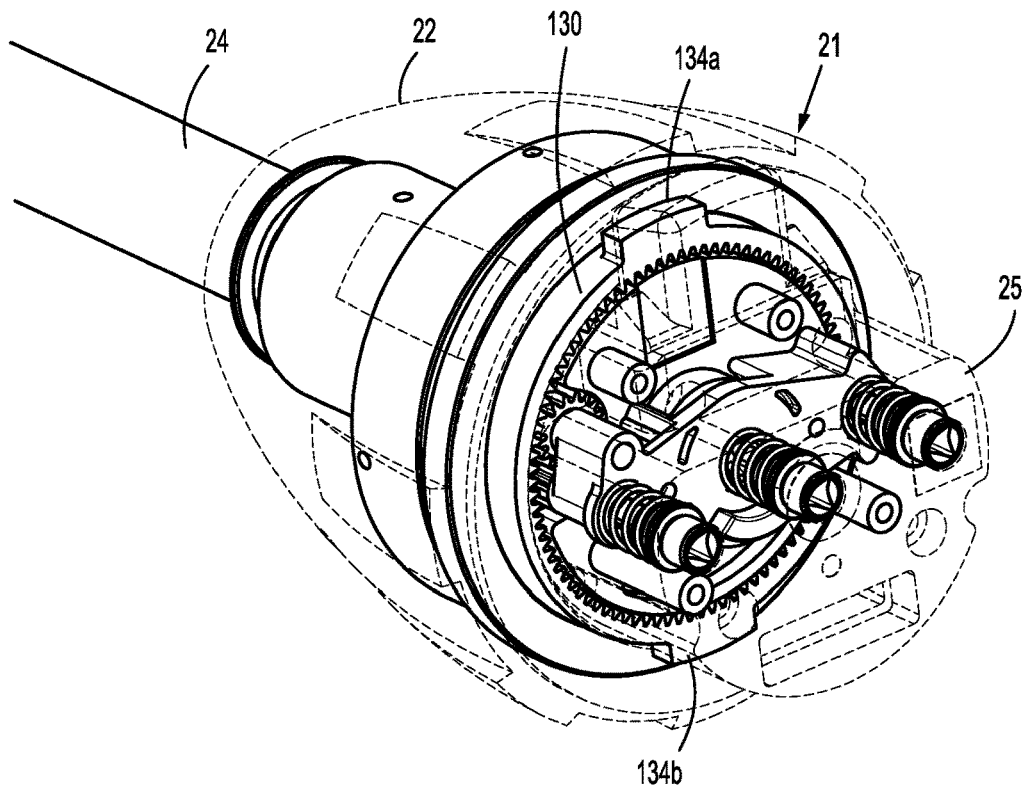
FIG. 17 is a rear, perspective view of the adapter assembly of FIG. 1A, with the outer housing shown in phantom.
Figure 18:
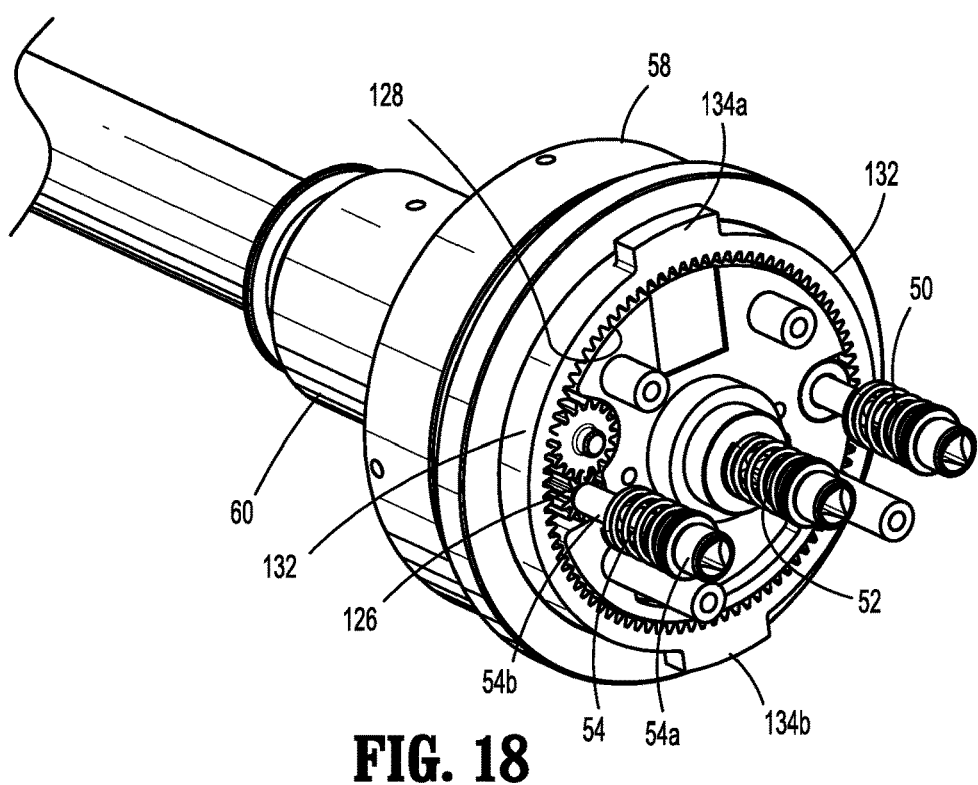
FIG. 18 is a rear, perspective view of internal components of the adapter assembly of FIG. 17.

With reference to FIGS. 17 and 18, the rotation mechanism of the adapter assembly 20 will now be described. The rotation input shaft 54 of the adapter assembly 20 has a proximal end portion 54a configured to be drivingly coupled to a drive member 13c of the handle assembly 12 to drive a rotation of the rotation input shaft 54. The rotation input shaft 54 has a gear 126 fixed about a distal end portion 54b thereof. The gear 126 of the rotation input shaft 54 is operably coupled to teeth 128 of a rotation ring gear 130 via an idler gear 132. In embodiments, the gear 126 of the rotation input shaft 54 may directly interface with the rotation ring gear 130.

The rotation ring gear 130 has a pair of tabs 134a, 134b extending radially outward from opposite radial positions of the rotation ring gear 130. The tabs 134a, 134b of the rotation ring gear 130 interlock with corresponding recesses (not explicitly shown) defined in an inner surface of the knob housing 22, such that the knob housing 22 is rotatable with the rotation ring gear 130 relative to the coupling mechanism 25. In embodiments, the rotation ring gear 130 may have any suitable feature that fastens the rotation ring gear 130 to the knob housing 22, such as, for example, threaded engagement, frictional engagement, lock and key engagement, latches, buttons, bayonet-type connections, welding, adhesives and/or other mechanisms.

In operation, to rotate the surgical loading unit 30, the rotation input shaft 54 is rotated via an actuation of the handle assembly 12 attached to the coupling mechanism 25 of the adapter assembly 20. Rotational motion of the rotation input shaft 54 is transferred to the rotation ring gear 130 via the idler gear 132. Since the tabs 134a, 134b of the rotation ring gear 130 lock the knob housing 22 thereto, rotation of the rotation ring gear 130 results in a rotation of the knob housing 22 relative to the coupling mechanism 25 and around the input shafts 50, 52, 54. The outer tube 24 of the adapter assembly 20 is fastened to the knob housing 22 and, as such, rotates with the knob housing 22, which, in turn, causes the surgical loading unit 30 to rotate about the longitudinal axis of the adapter assembly 20.

Persons skilled in the art will understand that the adapter assemblies and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly, comprising:
   a first input shaft;
   a cam housing operably coupled to the first input shaft and defining a proximal cam slot and a distal cam slot, the cam housing being configured to rotate;
   a first elongate shaft having a proximal end portion received in the proximal cam slot, and a distal end portion configured to be coupled to a surgical loading unit; and
   a second elongate shaft having a proximal end portion received in the distal cam slot, and a distal end portion configured to be coupled to the surgical loading unit, wherein the first and second elongate shafts are configured to move in opposing first and second longitudinal directions in response to a rotation of the cam housing to articulate the surgical loading unit, wherein the proximal and distal cam slots are longitudinally spaced from one another such that at least a majority of the proximal cam slot is disposed proximally of a proximal end of the distal cam slot.

2. The adapter assembly according to claim 1, wherein the proximal cam slot has one of a right-handed helical configuration or a left-handed helical configuration, and the distal cam slot has the other of the right-handed helical configuration or the left-handed helical configuration.

3. The adapter assembly according to claim 1, further comprising:
   a first link having a proximal end portion pivotably coupled to a distal end portion of the first elongate shaft, and a distal end portion configured to be pivotably coupled to the surgical loading unit; and
   a second link having a proximal end portion pivotably coupled to a distal end portion of the second elongate shaft, and a distal end portion configured to be pivotably coupled to the surgical loading unit, such that the first and second links articulate the surgical loading unit in response to an actuation of the first input shaft.

4. The adapter assembly according to claim 1, wherein the first and second elongate shafts are disposed on opposite sides of a central longitudinal axis defined by the cam housing.

5. The adapter assembly according to claim 1, wherein the cam housing includes a tubular shaft defining a longitudinally-extending channel, the proximal and distal cam slots defined in the tubular shaft.

6. The adapter assembly according to claim 5, wherein the proximal and distal cam slots are disposed around a central longitudinal axis defined by the tubular shaft of the cam housing.

7. The adapter assembly according to claim 1, further comprising a ring gear having an inner surface defining a plurality of gear teeth that are operably coupled to the first input shaft and fixed to the cam housing, such that a rotation of the first input shaft results in a rotation of the cam housing.

8. The adapter assembly according to claim 7, further comprising a spur gear cluster operably coupling the ring gear and the first input shaft.

9. The adapter assembly according to claim 1, wherein the first elongate shaft has a pin extending laterally from the proximal end portion thereof into the proximal cam slot, and the second elongate shaft has a pin extending laterally from the proximal end portion thereof into the distal cam slot.

10. The adapter assembly according to claim 1, further comprising:
   an outer housing having the first input shaft and the cam housing rotationally supported therein; and
   an outer tube extending distally from the outer housing, the outer tube having the first and second elongate shafts axially supported therein.

11. The adapter assembly according to claim 1, further comprising a second input shaft extending through the cam housing and configured to effect a clamping and firing of the surgical loading unit.

12. The adapter assembly according to claim 11, further comprising:
   a nut disposed within the cam housing and threadedly coupled to the second input shaft; and
   a knife shaft having a proximal end portion coupled to the nut and a distal end portion configured to cut tissue, wherein the nut is configured to distally move the knife shaft in response to a rotation of the second input shaft.

13. The adapter assembly according to claim 12, further comprising a firing rod having a proximal end portion fixed to the nut, and a distal end portion fixed to the proximal end portion of the knife shaft, wherein the second input shaft extends through the firing rod.

14. A surgical instrument, comprising:
   an adapter assembly including:
      a first axially movable elongate shaft;
      a second axially movable elongate shaft;
      a first link having a proximal end portion pivotably coupled to a distal end portion of the first elongate shaft; and
      a second link having a proximal end portion pivotably coupled to a distal end portion of the second elongate shaft, the first link including an inner surface facing the second link and having a concave intermediate portion;
   a surgical loading unit having a proximal end portion pivotably coupled to a distal end portion of the first link and a distal end portion of the second link, such that the first and second links articulate the surgical loading unit in response to longitudinal motion of the first and second elongate shafts; and
   an axially movable I-beam assembly disposed between the first and second links, wherein the concave intermediate portion of the inner surface of the first link contacts a first lateral side of the I-beam assembly upon the surgical loading unit articulating relative to the adapter assembly in a first direction.

15. The surgical instrument according to claim 14, wherein the inner surface of the first link has a convex proximal end portion and a convex distal end portion, the concave intermediate portion being disposed between the convex proximal and distal end portions of the inner surface.

16. The surgical instrument according to claim 14, wherein the surgical loading unit includes:
   an anvil plate; and
   a staple cartridge chassis pivotably coupled to the anvil plate, the I-beam assembly having a distal end portion slidably coupled to both the anvil plate and the staple cartridge chassis, such that distal movement of the I-beam assembly pivots the staple cartridge chassis toward the anvil plate.

17. The surgical instrument according to claim 14, wherein the second link includes an inner surface facing the first link and having a concave intermediate portion dimensioned to receive a second lateral side of the I-beam assembly upon the surgical loading unit articulating relative to the adapter assembly in a second direction, opposite the first direction.

* * * * *